US010144914B2

(12) United States Patent
Bookbinder et al.

(10) Patent No.: US 10,144,914 B2
(45) Date of Patent: Dec. 4, 2018

(54) MODIFIED SUBSTRATES FOR PROTECTION OF PEPTIDE-IMMOBILIZED SURFACES FROM GAMMA RADIATION DEGRADATION (75) Inventors: Dana Craig Bookbinder, Corning, NY (US); Arthur Winston Martin, Horseheads, NY (US); Santona Pal, Painted Post, NY (US); Christopher Bankole Shogbon, Corning, NY (US); Jennifer L. Weber, Big Flats, NY (US); Yue Zhou, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 338 days.

(21) Appl. No.: 13/032,166

(22) Filed: Feb. 22, 2011

(65) Prior Publication Data

US 2011/0207219 A1 Aug. 25, 2011

Related U.S. Application Data (60) Provisional application No. 61/307,126, filed on Feb. 23, 2010.

(51) Int. Cl.
*C12N 5/00* (2006.01)
(52) U.S. Cl.
CPC ........ *C12N 5/0068* (2013.01); *C12N 2533/20* (2013.01); *C12N 2533/50* (2013.01)
(58) Field of Classification Search
CPC .......... C12M 3/00; C07K 17/02; C07K 17/08; C12N 5/00; C12N 5/06; C12N 11/02; C12N 11/08
See application file for complete search history.

(56) References Cited

U.S. PATENT DOCUMENTS

| 2,832,689 | A | 4/1958 | Proctor | 99/157 |
|---|---|---|---|---|
| 4,999,297 | A | 3/1991 | Minoura et al. | 435/240.23 |
| 5,283,034 | A | 2/1994 | Okrongly et al. | 422/22 |
| 5,362,442 | A | 11/1994 | Kent | 422/22 |
| 5,534,254 | A | 7/1996 | Huston et al. | 424/135.1 |
| 5,837,846 | A | 11/1998 | Huston et al. | 536/23.53 |
| 5,981,163 | A | 11/1999 | Horowitz et al. | 435/4 |
| 6,017,543 | A * | 1/2000 | Salk et al. | 424/208.1 |
| 6,171,549 | B1 | 1/2001 | Kent | 422/22 |
| 6,479,533 | B1 * | 11/2002 | Yarosh | 514/398 |
| 6,787,179 | B2 | 9/2004 | Timm et al. | 427/2.24 |
| 7,252,799 | B2 | 8/2007 | Miekka et al. | 422/22 |
| 7,291,596 | B2 | 11/2007 | Hobson et al. | |
| 2003/0031584 | A1 | 2/2003 | Burgess et al. | 422/22 |
| 2003/0175408 | A1 | 9/2003 | Timm et al. | 427/2.1 |
| 2005/0106728 | A1 | 5/2005 | Burgess et al. | 435/440 |
| 2006/0002985 | A1 * | 1/2006 | Zicker | A61K 31/198 424/442 |
| 2006/0280645 | A1 * | 12/2006 | Sellers et al. | 422/22 |
| 2009/0036350 | A1 * | 2/2009 | Austin et al. | 514/2 |
| 2009/0081797 | A1 * | 3/2009 | Fadeev et al. | 436/86 |
| 2009/0191632 | A1 | 7/2009 | Fadeev et al. | 435/395 |
| 2009/0227024 | A1 | 9/2009 | Baker et al. | 435/378 |

FOREIGN PATENT DOCUMENTS

| EP | 1 757 680 | 2/2007 |
|---|---|---|
| EP | 1 852 443 | 11/2007 |
| JP | 08205893 A | 8/1996 |
| JP | 2000-169499 | 6/2000 |
| WO | 2004/009143 | 1/2004 |
| WO | 2007/136354 | 11/2007 |

OTHER PUBLICATIONS

CC, Covalent Coupling, Tech Note, Bangs Laboratories, Apr. 24, 2006.*
Levine et al., Methionine residues may protect proteins from critical oxidative damage, Mechanisms of Ageing and Development 107 (1999) 323-332.*
Zhao, J. M., et al., "Modification of Ti implant surface for cell proliferation and cell alignment", Journal of Biomedical Materials Research Part A, vol. 84A, No. 4, Mar. 15, 2008, pp. 988-993.
Steffens, G.C.M., et al., "High density binding of proteins and peptides to poly(D,L-lactide) grafted with polyacrylic acid", Biomaterials, vol. 23, No. 16, Aug. 1, 2002, pp. 3523-3531.
"Protein Stabilization Challenges: Solutions for In Vitro Applications", © 2008 SurModics, Inc.
Perlin, L., et al., "Production and performance of biomaterials containing RGD peptides", Soft Matter 2008, 4, , pp. 2331-2349.
Levine, Rodney L., et. al., "Methionine residues as endogenous antioxidants in proteins", Proc. Natl. Acad. Sci., USA, vol. 93, pp. 15036-15040, Dec. 1996, Biochemistry.

(Continued)

*Primary Examiner* — Taeyoon Kim
*Assistant Examiner* — Srikanth Patury
(74) *Attorney, Agent, or Firm* — Susan S. Wilks (57) ABSTRACT In the present specification and claims, three modified cell culture substrates are disclosed for protecting peptide mimetic surfaces used in cell culture technology. The methods are able to retain the functionality of the bioactive species conjugated to the surface. In particular, a vitronectin peptide fragment Ac-Lys-Gly-Gly-Pro-Gln-Val-Thr-Arg-Gly-Asp-Val-Phe-Thr-Met-Pro-NH2 was able to facilitate growth and proliferation of undifferentiated human embryonic stem cells after stabilization using 3 different modified cell culture substrates for of protection against gamma irradiation. The modified substrates disclosed in this invention are (i) covalent attachment of the antioxidant molecules (via blocking step); (ii) The use of coatings consisting of anti-oxidants and stabilizers comprising glycoprotiens, sugars, carbohydrates, poly(amino acids), peptides and hydrophilic polymers; and (iii) a third method wherein the same methionine contained in the bioactive sequence used to facilitate growth and proliferation of human embryonic stem cells was also used as a sacrificial coating to protect the same conjugated sequence against damage by gamma irradiation.

15 Claims, 6 Drawing Sheets

Specification includes a Sequence Listing.

(56) References Cited

OTHER PUBLICATIONS

Melkani, G.C., "Protection of GroEL by its methionine residues against oxidation by hydrogen peroxide", Biochemical and Biophysical Research Communications 347, 2006, pp. 534-539.

Bourdon, E., et al., "Differential effects of cysteine and methionine residues in the antioxidant activity of human serium albumin", Free Radical Research, Jan. 2005, 39(1), pp. 15-20.

Lam*, X. M., "Antioxidants for prevention of methionine oxidation in recombinant monoclonal antibody HER2", Journal of Pharmaceutical Sciences, vol. 86, No. 11, Nov. 1997, pp. 1250-1255.

Translation of Official Action; Japanese Application No. 2012-555045; OA dated Feb. 2, 2016; pp. 1-10.

Patent Cooperation Treaty International Search Report; International Searching Authority; dated Oct. 7, 2011; PCT Application No. PCT/US2011/025138; pp. 1-7.

\* cited by examiner

MODIFIED SUBSTRATES FOR PROTECTION OF PEPTIDE-IMMOBILIZED SURFACES FROM GAMMA RADIATION DEGRADATION

CLAIMING BENEFIT OF PRIOR FILED U.S. APPLICATION

This application claims the benefit of U.S. Provisional Application Ser. No. 61/307,126, filed on Feb. 23, 2010, hereby incorporated by reference in its entirety.

FIELD

Modified cell culture substrates are disclosed that protect and stabilize against degradation of unmodified cell culture substrates by sterilizing gamma irradiation. Sterilization of biological cell culture surfaces reduce the level of active biological contaminants or pathogens. These modified substrates are comprised of stabilizers and antioxidants.

This application contains a Sequence Listing electronically submitted via EFS-Web to the United States Patent and Trademark Office as text filed named "Seq_ST25.txt" having a size of 1 kb and created on 5/3/11. Due to the electronic filing of the Sequence Listing, the electronically submitted Sequence Listing serves as both the paper copy required by 37 CFR § 1.821(c) and the CRF required by § 1.821(e). The information contained in the Sequence Listing is hereby incorporated herein by reference.

BACKGROUND

Many biological materials that are prepared for human, veterinary, diagnostic and/or experimental use may contain unwanted and potentially dangerous biological contaminants or pathogens, such as viruses, bacteria, nanobacteria, yeasts, molds, mycoplasmas, ureaplasmas, prions and parasites. Consequently, it is of utmost importance that any biological contaminant in the biological material be inactivated before the product is used. This is critical for the various biological materials that are prepared in media or via culture of cells or recombinant cells which may be subject to mycoplasma, prion, bacterial and/or viral contaminants.

Peptide-immobilized surfaces have been broadly used to mimic extracellular proteins (such as fibronectin, collagen, vitronectin and lamininin) in the design of scaffold for use in tissue engineering to promote mammalian cell adhesion, proliferation and differentiation. However, in order for these peptide mimetic surfaces to have any therapeutic value they must be sterilized to achieve a sterilization assurance level (SAL) of $10^{-6}$, which is the probability of one in a million items being non-sterile.

A conventional method for assuring sterility of a biological production process is aseptic manufacturing. The demands of maintaining a sterile environment throughout this manufacturing process are time-consuming, laborious, and extremely expensive. There are also other sterilization methods to choose from, such as ethylene oxide (EtO), E-beam and Gamma radiation. Ethylene oxide, while being a highly effective method, but leaves behind potentially hazardous residuals and can not reach products in airtight packages. E-beam, while being one of the fastest methods for sterilization, can not penetrate well into dense products or bulk packaging of some products.

Gamma radiation does have some significant advantages over other methods of producing sterile product, such as (1) better assurance of product sterility than aseptic manufacturing; (2) no residue like EtO leaves behind; (3) More penetrating than E-beam; (4) Low-temperature process; (5) Simple validation process. Gamma radiation can also have harmful effects on biological materials, such as proteins or peptides because of free radical formation. Peptide conjugated surfaces have been developed which for the first time provide support for embryonic stem cell proliferation and differentiation in chemically defined media. However, studies showed that after gamma sterilization, the performance of those surfaces were harmed.

In view of the difficulties discussed above, there remains a need for methods of sterilizing cell culture surface compositions or materials that are effective for reducing the level of active biological contaminants or pathogens without an adverse effect on the surface composition or materials.

SUMMARY

The specification and claims of the present application disclose modified cell culture substrates for sterilizing peptide mimetic cell culture substrates in achieving a (SAL) Sterilization Assurance Level of $10^{-6}$, therein, one microbe per million items is present. Three modified cell culture substrates are disclosed and claimed to protect a peptide mimetic surface against gamma irradiation when used as a form of sterilization.

In one embodiment, antioxidant molecules, such as vitamins, amino acids, derivatives of amino acids and short chain peptides have been proposed as blocking reagents (to deactivate reactive groups) during peptide conjugation to protect peptides through gamma sterilization. For example, using primary amines containing antioxidant molecules, such as a methionine derivative, as a blocking reagent (quenching of un-reacted NHS ester) during the peptide conjugation process using ethyl (dimethylaminopropyl) carbodiimide (EDC)/N-Hydroxysuccinimide (NHS) method was demonstrated to be quite successful. For other conjugation mechanisms, different groups suitable for the deactivation of reactive groups may be needed in the antioxidant molecules. This modified substrate of protecting peptide conjugated surfaces during the exposure to gamma irradiation for terminal sterilization has not been previously reported. An advantage of this modified substrate is gained by not having a preparative step prior to culturing (i.e., washing prior to cell culturing is not required in this embodiment). This modification and resulting substrate will potentially provide universal methods to protect any peptide on conjugated surfaces during gamma sterilization, manufacturing process or storage.

A second embodiment disclosed in the specification and claims of the present application relates to sacrificial coatings comprising of anti-oxidants and stabilizers of sugars, carbohydrates, small organics, glycoproteins, vitamins, amino acid salts, derivatives of amino acids, short chain peptides, glycoproteins and proteins have been proposed. Other additional stabilizers selected from the group consisting of: ascorbic acid or a salt or ester thereof; glutathione; 6-hydroxy-2,5,7,8-tetramethylchroman-2-carboxylic acid; uric acid or a salt or ester thereof; methionine; histidine; N-acetyl cysteine; diosmin; silymarin; lipoic acid; sodium formaldehyde sulfoxylate; gallic acid or a derivative thereof; propyl gallate; a mixture of ascorbic acid, or a salt or ester thereof, and uric acid, or a salt or ester thereof; a mixture of ascorbic acid, or a salt or ester thereof, and 6-hydroxy-2,5,7,8-tetramethylchroman-2-carboxylic acid; a mixture of ascorbic acid, or a salt or ester thereof, uric acid, or a salt or ester thereof, and 6-hydroxy-2,5,7,8-tetramethylchroman-2- carboxylic acid; and a mixture of uric acid, or a salt or ester thereof and 6-hydroxy-2,5,7,8-tetramethylchroman-2-carboxylic acid. Other bioactive coatings include heparin, phosphoryl choline, urokinase or rapamycin. In addition, the bioactive coating can be selected from hydrophilic and hydrophobic coatings comprising of polylactic acid, polyglycolic acid, polycaprolactone, polyparadioxanone, polytrimethylene carbonate and their copolymers, collagen, elastin, chitin, coral, hyaluronic acid. Still other polymers include polyvinyl pyrrolidone, polyethylene glycol, polypropylene glycol, polyethylene glycol-co-propylene glycol, polyethylene glycol acrylate, polyethylene glycol diacrylate, polyethylene glycol methacrylate, polyethylene glycol dimethacrylate, polyethylene oxide, polyvinyl alcohol, polyvinyl alcohol-co-vinylacetate, polyhydroxyethyl methacrylate, and polyhyaluronic.

Cell morphology, distribution, and relative number (assessed via crystal violet, CV staining) on gamma-irradiated peptide acrylate surfaces with anti-oxidant coatings 2, 3, 4, 6, and 8 were comparable to that of those cells cultured on ethanol sanitized and Matrigel™ controls at day 2. Cells did not attach to, nor had embryoid body (EB) like morphology on, gamma-IR peptide acrylate surface with-coatings 1, 5, and 7. Coatings 9 and 10 are expected to show similar performance as 2, 3, 4, 6 and 8. See Table 1 below for a description of the coatings content. Antioxidants with opposite charge of that of the surface being protected help increase the absorption and uniform distribution of said agent. As an example, methionine derivative, such as methionine ester, which contain positive charge and help absorption of this molecule to negative charged peptide acrylate surfaces. Result has demonstrated the efficiency in protection of peptide conjugated surfaces during gamma sterilization using this strategy.

In a third embodiment, an adhesive peptide containing methionine residue can be successfully used as a protective coating to protect the same conjugated methionine containing peptide that could not withstand gamma irradiation in the conjugated state under similar conditions. The vitronectin peptide sequence was successful in stabilizing the coatings against gamma irradiation and result in successful cell response.

The mechanism for stabilization may be related to antioxidants and stabilizers as scavengers for free radicals. Furthermore, stabilizers serve to protect bioactive molecules by forming ionic bonds and/or weak Vander Waals forces which may make the peptides more resistant to oxidation and therefore allow them to maintain their integrity after gamma irradiation. The modified substrates described herein are specific to protecting bioactive cell culture substrates used for in vitro cell culture.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description of the preferred embodiments which follow.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to".

The term "hydrogel" has been used to describe cell culture surfaces. "Hydrogel" has been variously defined to include a gel or gelatin that can absorb water in an amount greater than or equal to 30% or up to 10,000% of its dry weight. Hydrogels have been classified according to water content. For example, hydrogels have been described as absorbing 30% water or more. When contacted with water, hydrogels swell but do not dissolve. The term "hydrogel" is a very broad term, describing a wide range of materials, including acrylates, having a wide range of water swelling and water absorbing characteristics.

As used herein, the term "sterilize" is intended to mean a reduction in the level of at least one active or potentially active biological contaminant or pathogen found in the biological cell culture substrate being treated according to the present invention. Terminal sterilization refers to exposure to sterilizing agents such as gamma ionizing radiation after assembly. Terminal sterilization is more desirable than aseptic manufacturing because it is very expensive to implement aseptic manufacturing on a large scale and it is prone to ongoing contamination issues. Radiation in the gamma frequency range ($>3\times10^{19}$ Hz) penetrates packaging materials and can be applied on large scale at ambient temperatures. Gamma irradiation is typically used for sterilizing cell culture ware after packaging. Depending upon the bioburden of each process and product, a sterility assurance level (SAL) of $10^{-3}$ is typically expected for cell culture products.

As used herein, the term "sulphur-containing amino acid: is intended to mean an amino acid residue containing the element, sulphur (i.e., methionine (M) and cysteine (C).

As used herein, the term "biological contaminant or pathogen" is intended to mean a contaminant or pathogen that, upon direct or indirect contact with a biological cell culture substrate, may have a deleterious effect on a biological cell culture substrate. Such biological contaminants or pathogens include the various viruses, prions, molds, yeasts, bacteria, nanobacteria, mycoplasmas, ureaplasmas and parasites known to those of skill in the art to generally be found in or infect biological materials. Examples of biological contaminants or pathogens include, but are not limited to, the following: viruses, such as human immunodeficiency viruses and other retroviruses, herpes viruses, filoviruses, circoviruses, paramyxoviruses, cytomegaloviruses, hepatitis viruses (including hepatitis A, B and C and variants thereof), pox viruses, toga viruses, Ebstein-Barr viruses and parvoviruses; bacteria, such as *Escherichia, Bacillus, Campylobacter, Streptococcus* and *Staphalococcus*; nanobacteria; parasites, such as *Trypanosoma* and malarial parasites, including *Plasmodium* species; yeasts; molds; mycoplasmas; ureaplasmas; and prions responsible for TSE (transmissible spongiform encephalopathies), such as scrapie, kuru, BSE (bovine spongiform encephalopathy), CJD (Creutzfeldt-Jakob disease), Gerstmann-Straeussler-Scheinkler syndrome and fatal familial insomnia. As used herein, the term "active biological contaminant or pathogen" is intended to mean a biological contaminant or pathogen that is capable of causing a deleterious effect, either alone or in combination with another factor, such as a second biological contaminant or pathogen or a native protein (wild-type or mutant) or antibody, in the biological material and/or a recipient thereof.

As used herein, the phrase "to protect and stabilize" is intended to mean to reduce any damage to the biological material being irradiated, that would otherwise result from the irradiation of that material, to a level that is insufficient to preclude the safe and effective use of the material following irradiation. In other words, a substance or process "protects and stabilizes" a biological material from radiation if the presence of that substance or carrying out that process results in less damage to the material from irradiation than in the absence of that substance or process. Thus, biological material may be used safely and effectively after irradiation in the presence of a substance or following performance of a process that "protects and stabilizes" the material, but could not be used safely and effectively after irradiation under identical conditions but in the absence of that substance or the performance of that process.

The specification and claims of the present application relate to modified substrates for sterilizing peptide mimetic cell culture substrates for achieving an SAL of $10^{-6}$. Three modified cell culture substrates are described to protect a peptide mimetic surface against gamma irradiation when used as a form of sterilization.

In one disclosed method, antioxidant molecules, such as vitamins, amino acids, amino acid derivatives and short chain peptides have been proposed as blocking reagents (to deactivate the reactive groups) during the peptide conjugation to protect the peptide during gamma sterilization. For example, using amines containing antioxidant molecules, such as a methionine derivative, as a blocking reagent (quenching of un-reacted Hydroxysuccinimide ester) during the peptide conjugation process using ethyl (dimethylaminopropyl) carbodiimide (EDC)/N-Hydroxysuccinimide (NHS) method was demonstrated to be quite successful. For other conjugation mechanisms, different groups suitable for the deactivation of reactive groups may be needed in the antioxidant molecules. Using this method to protect peptide conjugated surfaces during gamma irradiation exposure for terminal sterilization has not yet been reported. An advantage of this method compared with physical absorbance or mixing is to have a non-preparative step prior to culturing, i.e., washing prior to cell culture is not required because antioxidant molecules will not be released from the surface as extractables.

Methionine is an amino acid in proteins which can easily be oxidized. If methionine is important for the protein function, the oxidization could lead to damage or loss of the intended biological function. Methionine has also been used by proteins or cells as an antioxidant defense system or being added in formulation to protect proteins or other biological products from being damaged by gamma irradiation or even during storage. Short peptides with multiple methionine units are capable of active oxygen inhibition for the treatment of arthritis, rheumatoid arthritis, Behcet's disease, cardiac infarction, etc. Using short peptide with methionine or multiple methionine residues for the conjugation may further improve the efficiency.

Short peptide chains comprising methionine may also comprise lysine, which may be conjugated to the surface of the substrate through, for example, amine reactive groups. Short peptide chains may comprise 1 to 4 methionine residues. Examples of short peptide chains comprising methionine and lysine include: Lys-Met, Lys-Met-Met, Lys-Met-Met-Met, and Lys-Met-Met-Met-Met.

The advantages of this modified substrate include:
1) Covalent attachment prevents phase separation or crystallization of antioxidants, which ensures uniform distribution and efficiency for the protection;
2) No additional step is needed in the conjugation process;
3) Antioxidant molecules are closer to its protection target. This will further increase protection efficiency;
4) The antioxidant molecules are covalently attached to the surface, therefore no extractables are introduced and no additional washing is needed before cell culture; and
5) Universally allows various types of peptide conjugated surfaces to be protected during gamma sterilization, as well as process stress and long term storage.

In the second modified substrate cell culture disclosed in the present specification and claims, sacrificial coatings comprising of anti-oxidants and sugar stabilizers, carbohydrates, small organics, glycoproteins, vitamins, amino acid salts, derivatives of amino acids, short chain peptides, glycoproteins and proteins have been proposed. Additional stabilizers selected from the group consisting of: ascorbic acid or a salt or ester thereof; glutathione; 6-hydroxy-2,5,7,8-tetramethylchroman-2-carboxylic acid; uric acid or a salt or ester thereof; methionine; histidine; N-acetyl cysteine; diosmin; silymarin; lipoic acid; sodium formaldehyde sulfoxylate; gallic acid or a derivative thereof; propyl gallate; a mixture of ascorbic acid, or a salt or ester thereof, and uric acid, or a salt or ester thereof; a mixture of ascorbic acid, or a salt or ester thereof, and 6-hydroxy-2,5,7,8-tetramethylchroman-2-carboxylic acid; a mixture of ascorbic acid, or a salt or ester thereof, uric acid, or a salt or ester thereof, and 6-hydroxy-2,5,7,8-tetramethylchroman-2-carboxylic acid; and a mixture of uric acid, or a salt or ester thereof and 6-hydroxy-2,5,7,8-tetramethylchroman-2-carboxylic acid was disclosed. Bioactive coatings comprised of heparin, phosphoryl choline, urokinase or rapamycin also can be used. In addition, the bioactive coating is selected from hydrophilic and hydrophobic coatings comprising of polylactic acid, polyglycolic acid, polycaprolactone, polyparadioxanone, polytrimethylene carbonate and their copolymers, collagen, elastin, chitin, coral, hyaluronic acid. Other polymers cited are polyvinyl pyrrolidone, polyethylene glycol, polypropylene glycol, polyethylene glycol-co-propylene glycol, polyethylene glycol acrylate, polyethylene glycol diacrylate, polyethylene glycol methacrylate, polyethylene glycol dimethacrylate, polyethylene oxide, polyvinyl alcohol, polyvinyl alcohol-co-vinylacetate, polyhydroxyethyl methacrylate, and polyhyaluronic. Other surface stabilizing agents can be HSA, BSA, ovalbumin, or collagen, or a glycoprotein combined with an oxygen radical scavenger that is a di- or polysaccharide or in a reduced form.

The advantages of this modified substrate include:
1. Anti-oxidants and stabilizers can serve as ubiquitous protective layers, i.e., can protect all biological ligands, including peptides and recombinant ECM proteins from terminal sterilization which will include gamma irradiation;
2. Universally allow various types of peptide conjugated surfaces to be protected during gamma sterilization and long term storage;
3. Anti-oxidants and stabilizers can be combined to improve function and cost effectiveness;
4. Thin coatings may not need to be removed or can easily be removable by dissolving in water without toxic effect to cells; and
5. Minimal costs will be added to total manufacturing cost.

In the third modified cell culture substrate disclosed in the specification and claims of the present application, an adhesive peptide containing methionine residue can be successfully used as a protective coating to protect the same conjugated methionine containing peptide that could not withstand gamma irradiation in the conjugated state under similar conditions.

The advantages of this modified substrate include:
1. A re-vamped GMP validation will not be required because the peptides used as sacrificial layer and removed before cell culture will be the same as conjugatible peptide;
2. Adhesive peptide coating will be applied at low concentration in very thin coating to reduce cost impact;
3. Adhesive peptide will be easily removed; and
4. Adhesive peptide can be used as a universal protecting agents against gamma irradiation.

According to the modified substrates disclosed herein, the cell culture surface to be sterilized is irradiated with the radiation for a time effective for the inactivation of one or more active biological contaminants or pathogens in the cell culture surface. Combined with irradiation rate, the appropriate irradiation time results in the appropriate dose of irradiation being applied to the culture surface. Suitable irradiation times may vary depending upon the particular form and rate of radiation involved, the nature and characteristics of the particular surface being irradiated and/or the particular biological contaminants or pathogens being inactivated. Suitable irradiation times can be determined empirically by one skilled in the art.

According to the modified substrates of the present invention, the cell culture surface to be sterilized is irradiated with radiation up to a total dose effective for the inactivation of one or more active biological contaminants or pathogens in the surface, while not producing an unacceptable level of damage to that surface. Suitable total doses of radiation may vary depending upon certain features of the methods being employed, such as the nature and characteristics of the particular cell culture surface being irradiated, the particular form of radiation involved and/or the particular biological contaminants or pathogens being inactivated. Suitable total doses of radiation can be determined empirically by one skilled in the art. The total dose of radiation can be at least 10 kGy or more.

The particular geometry of the cell culture surface being irradiated, such as the thickness and distance from the source of radiation, may be determined empirically by one skilled in the art.

According to the modified cell cultures disclosed in the present application, the irradiation of the cell culture surfaces may occur at any temperature which is not deleterious to the surfaces being sterilized. Accordingly, the cell culture surface can be irradiated at ambient temperature. Alternatively, the cell culture surface is irradiated at reduced temperatures, i.e. a temperature below ambient temperature, such as 0° C., or lower, etc.

According to another modified cell culture of the application, the cell culture surface is irradiated at elevated temperature, i.e. a temperature above ambient temperature, such as 37° C., or higher C, etc. While not wishing to be bound by any theory, the use of elevated temperature may enhance the effect of irradiation on the biological contaminant(s) or pathogen(s) and therefore allow the use of a lower total dose of radiation.

According to the modified cell cultures disclosed herein, the irradiation of the cell culture surface may occur at any pressure which is not deleterious to the surface being sterilized. Accordingly, the culture surface is irradiated at elevated pressures. The cell culture surface is irradiated at elevated pressure due to the application of sound waves. While not wishing to be bound by any theory, the use of elevated pressure may enhance the effect of irradiation on the biological contaminant(s) or pathogen(s) and therefore allow the use of a lower total dose of radiation.

Generally, according to the methods described herein, the pH of the cell culture surface undergoing sterilization is about 7. In some embodiments of the present invention, however, in order to avoid aggregation of the components of the surface or for other reasons, the culture surface may have a pH of less than 7 to a pH of 3. Alternatively, the cell culture surface may have a pH of greater than 7 m and up to 11.

EXEMPLIFICATION

The invention is further illustrated by the following non-limiting examples. Other suitable modifications and adaptations are of the variety normally encountered by those skilled in the art and are fully within the spirit and scope of the present invention.

Example 1: Use of Anti-oxidant Molecules as Blocking Agents for Protecting Peptide Mimetic Surface(s) During Gamma Sterilization Materials and Methods;

Acrylate coating: 2-Hydroxyethyl methacryalte, 2-carboxyethyl acrylate, tetra(ethylene glycol) dimethacrylate, Darocur 1173, Irgacure 819 were mixed with ratio of 80:20:3:3:0.1 and dissolved in ethanol at total monomer concentration of 5%. The obtained formulation was spin coated on oxygen plasma treated Zeonor film. After ethanol evaporated, the (meth)acrylate coating was cured using Xenon pulsed UV curing system in nitrogen purged box. Then, the coated films were in-mold-labeled into T-75 Zeonor flasks and used for conjugation directly.

Peptide conjugation: The acrylate surface was activated for an hour with 1:1 EDC: NHS in DMF. After aspiration of the activation solution, the surface was treated for an hour with 1 mM of the VN peptide (Ac-KGGPQVTRGD-VFTMP) (SEQ ID NO:1) in phosphate buffer (pH7.4). After aspiration of the peptide solution, the surface was treated for an hour with 1M ethanolamine adjusted to pH 8.0-8.5 with hydrochloric acid or 0.1M of L-methionine methyl ester hydrochloride adjusted to pH 8 with sodium hydroxide based on experimental design. All reactions were performed at room temperature.

Amino acid absorption: Peptide conjugated T-75 flask was filled with 10 mL of 0.1M of L-methionine methyl ester hydrochloride adjusted to pH 8 with sodium hydroxide. The flasks were lay flat so that the peptide surfaces were submerged under the amino acid solution and were incubated for 1 hr. This allows positive charged amino acid to be absorbed into negative charged peptide-acrylate coating. Then the amino acid solution was removed and the flasks were dried in vacuum for overnight before packing and sterilization.

Sterilization: Flasks were packed with nitrogen and desiccant in aluminum pouch for Gamma sterilization. The irradiation dose was 11-18 kGy. Positive control VN-peptide acrylate sample was sanitized with 70% ethanol.

Stem cell culture: H7 cells were sub-cultured into T-75 fasks with desired peptide acrylate surfaces or Matrigel™ coated surfaces (positive control) at the density of 100,000 cell/cm$^2$ in X-VIVO 10+GF medium. Microscopic examination of cell and colony morphology was performed at day 3 or day 4. Cell number was assessed at day 4 or day 5 by harvesting with collagenase IV/EDTA treatment followed by cell counting with automated cell number/viability analyzer, Vi-Cell (Beckman Coulter). For methionine methyl ester treated surface, a step of rinsing with DPBS was applied to remove amino acid extractables before cell culture.

Results and Discussion

Figure 1:
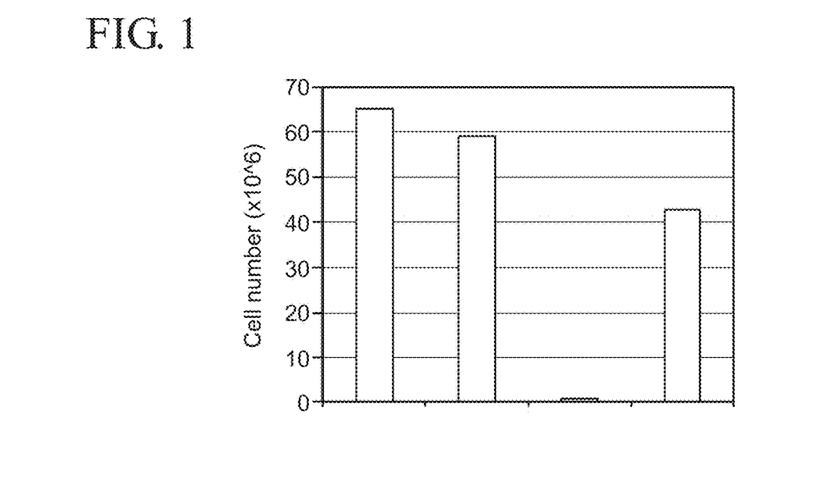
FIG. 1 is a bar graph illustrating Cell count of H7 after 4 day culture on VN peptide acrylate surfaces treated with methionine derivative (second bar) solution and controls (third bar); Cell count on VN-peptide conjugated acrylate surface without gamma sterilization (ETOH ctr—first bar) and on Matrigel surface (fourth bar) were used as positive controls; Cell count on VN peptide conjugated acrylate surface with gamma sterilization but without any treatment was used as negative control.
Figure 2A:
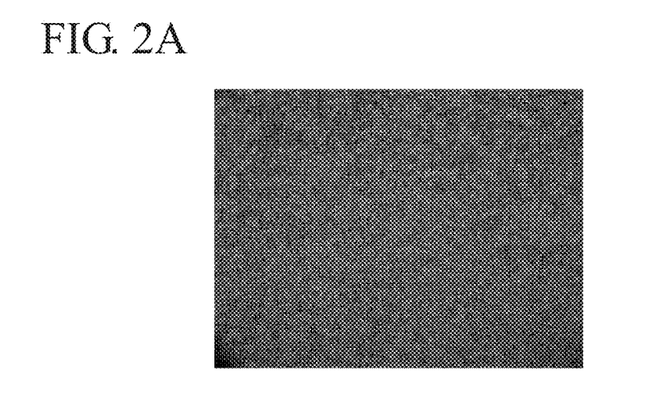
FIG. 2 presents photographic phase contrast images of H7 stem cell on VN peptide conjugated acrylate surface with out gamma irradiation (a) or on gamma sterilized surface which has been treated with methionine derivative before irradiation (b).
Figure 2B:
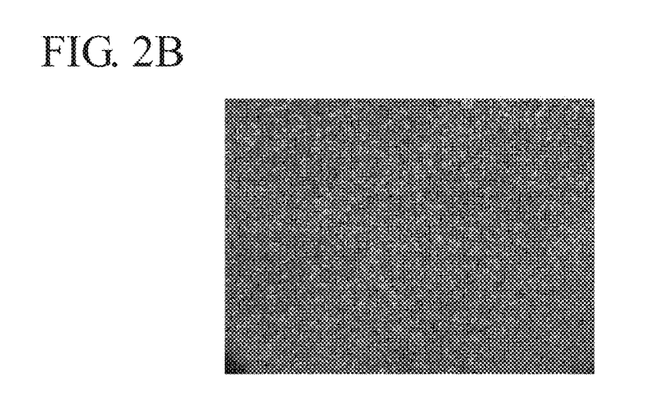

Amino acid absorption: Cell count after 4 days of culture was used to show the impact to bioactivity of peptide acrylate surface after Gamma sterilization. Without any treatment, H7 can not adhere to the Gamma irradiated VN-peptide surface as shown by "no treatment" in FIG. 1. While on methionine ester treated VN-peptide acrylate surface, the bioactivity was maintained after Gamma irradiation. This was demonstrated by comparable cell number on the surface treated with Methionine vs. that the surface without gamma irradiation (ETOH ctr) and Matrigel (our bench mark surface) as shown in FIG. 1. With methionine treatment the stem cell morphology was also comparable positive control.

Figure 3A:
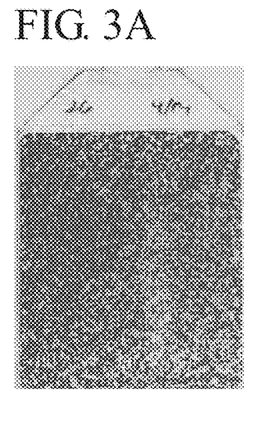
FIG. 3 presents photographs of crystal violet staining of H7 cells grown on VN peptide conjugated acrylate surfaces which has been blocked with ethanolamine (a,c) or methionine derivative (b). Flasks shown in (b) an (c) have been gamma sterilized while flask shown in (a) was sanitized with ethanol and used as positive control.
Figure 3B:
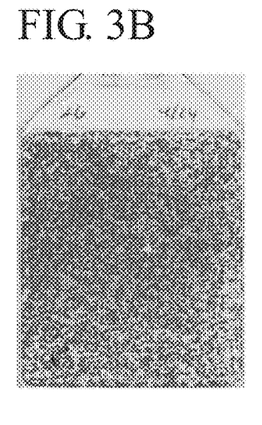
Figure 3C:
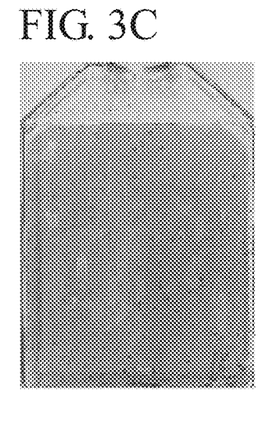

Amino acid blocking: methionine methyl ester was also used to replace traditional blocking reagent—ethanolamine to diactivate carboxyl-NHS ester after peptide conjugation. After gamma irradiation, VN-peptide acrylate surface which was blocked using methionine methyl ester still support good H7 attachment and growth as shown in FIG. 3 which was comparable to positive control surfaces. While, on the surface blocked with ethanolamine, there were not cells attached or grew (FIG. 3). Even thought cell morphology is still not able to much those on ethanol sanitized surfaces, we believe that this method can be combined with other process improvement to deliver Gamma sterilizable VN-peptide acrylate flasks.

Above results suggest that methionine and its derivative can be used to protect peptide conjugated surfaces during Gamma sterilization. To further increase the protection efficiency, short peptides with multiple methionine residuals may be used for surface treatment or blocking. These will increase the amount of methionine moiety incorporated into the system.

BSP has shown some unique properties for cardiovascular stem cell differentiation. However its bioactivity was significantly impacted by gamma irradiation based on our internal results. This makes it difficult to develop final production based on BSP peptide. Above strategies will potentially help to make gamma sterilizable BSP surfaces for stem cell culture.

Example 2: Gamma Irradiation Protective Coating for Peptide Mimetic Surface(s) Comprising Anti-Oxidants and Stabilizers Materials and Methods:

i) Preparation of acrylate coatings: All acrylate coatings were prepared as described above in Method 1. After preparation, all flasks were stored with caps on at room temperature until ready for use for peptide conjugation experiments.

ii) Conjugation of VAT peptides on acrylate surfaces: Procedure for peptide conjugation was described above in Method 1 and blocked with ethanolamine only. After peptide conjugation, all flasks were stored with caps on at room temperature until ready for various coating applications.

iii) Preparation of Antioxidant/Stabilizer Formulations: Prior to preparation of the antioxidant/stabilizer coating formulation, solubility of the individual components of each formulation was determined in water, ethanol and 1M HCl. Majority of the components were soluble in water, except for two in ethanol and one in 1M HCl. Both n-propyl gallate and Trolox were soluble in ethanol and only L-Tryptophan in 1M HCl. For each individual coating mixture formulation (i.e. Coatings 1-8), in a separate 25 mL glass vial containing the different components individually weighed out based on their respective wt % (see Table 1, below), Coating 1: 22 ml of solvent was used to make the coating solution (i.e. 20 mL of DI/water+2 ml of ethanol); Coating 2: 20 mL of DI/water added to vial; Coating 3: 18 mL of DI/water added+2 mL of ethanol to vial; Coating 4: 20 mL of DI/water+2 mL of ethanol; Coating 5: 16 mL of DI/water+4 mL of 1M HCl; Coating 6: 12 mL of DI/water+2 mL of ethanol+4 mL of 1M HCl; Coating 7: 20 mL of DI/water; Coating 8: 10 ml of DI/water+4 ml of ethanol+5 ml of 1M HCl.

TABLE 1

| Coating ID | Antioxidant composition (wt %) | Solvents Used. |
| --- | --- | --- |
| 1 | Human Serum Albumin: (0.2%); Sucrose:(4%); Hyaluronic acid: (0.2%); N-propyl gallate: (5%); | DI/water; Ethanol. |
| 2 | Human Serum Albumin: (0.2%); N-acetyl-L-cysteine (4%); L-tryptophan: (4%) Hyaluronic acid: (0.2%); L-sodium ascorbate (5%); | DI/water; 1M HCl*. |
| 3 | Human Serum Albumin: (0.2%); Trolox: (500 mg/4 mL): (4%); Dulcitol: (4%) Hyaluronic acid: (0.2%); L-Carnosine: (4%); | DI/water; Ethanol |
| 4 | Poly (Glu, Lys, Tyr) salt: (0.125%); N-acetyl-L-cysteine: (4%); D-Mannitol: (3%) Hyaluronic acid: (0.2%); N-propyl gallate: (5%); Heparin Sulphate: (0.025%) | DI/water; Ethanol |
| 5 | m-PEG amine: (3%); L-methionine: (4%); L-tryptophan: (4%)* Hyaluronic acid: (0.2%); Sucrose: (4%); | DI/water; 1M HCl*. |
| 6 | Trolox: (500 mg/4 ml); L-Tryptophan: (4%)*; N-acetyl-L-cysteine (4%) Hyaluronic acid: (0.2%); Leucrose: (4%); Polygalacturonic acid salt: (4%) | DI/water; Ethanol; 1M HCl*. |
| 7 | Sialic acid: (1%); Methionine: (4%); Phytic acid: (4%) Hyaluronic acid: (0.2%); Alginic acid salt: (1%); | DI/water; |
| 8 | Poly(acrylic acid Sodium phosphate monobasic: (4%)) Trolox: (500 mg/4 ml); L-Tryptophan: (4%)*; N-acetyl-L-cysteine: (4%) Hyaluronic acid: (0.2%); L-Methionine: (4%); L-Tryptophan (4%) | DI/water; Ethanol; 1M HCl*. |
| 9 | L-Anserine nitrate salt (0.2%); A-Lipoic acid (1%); Vitamin P (Rutin Hydrate): (4%); Morin Hydrate (2%); Estrone 3-sulfate sodium salt (2%). | DI/water; Ethanol. |
| 10 | L-(+)-Ergothioneine (0.2%); Sodium selenite pentahydrate (4%); Rebamipide hydrate: (2%); (−) Epigallocatechin gallate: (1%); Phosphomolybdic acid solution: (0.5%). | DI/water; Ethanol |

Table 1. A library showing different combinations of 10 antioxidant/stabilizer coating formulations used in this study along the solvents used to dissolve the formulations. Formulations 2, 3, 4, 6, and 8 were able to stabilize the vitronectin peptide sequence conjugated to the surface against gamma irradiation.

iv) Procedure for coating in Peptide Acrylate T-75 flasks: In a 25 mL glass vial containing each coating formulations dissolved in the appropriate solvent combinations, a volume between 18-22 mL of the solutions is dispensed into the corresponding flasks using a semi-automated pipette. The flask containing the solution is tilted back and forth a couple of times to ensure uniform coverage of the bottom of the flask with the coating. The flasks are then placed in a vacuum oven (at ~27 in Hg) containing a cold trap (with refrigeration), heated to about 30° C. and allowed to dry to ensure complete removal of any residual solvents present. The flasks are placed in the vacuum oven for at-least 4 days then placed in a nitrogen purge box until ready for packaging.

v) Packaging of samples for sterilization: Samples for Coatings 1 through 4 were packaged together under vacuum using a single Nylon pouch containing 4 desiccant packets and heat sealed. Coatings 5 and 8 were packaged together under vacuum in an aluminum pouch containing 4 desiccant packets and heat sealed. Lastly, Coating 6 and 7 were also packaged together under vacuum in an aluminum pouch containing 4 desiccant packets and heat sealed. A medical grade gas-vacuum sealer was used.

vi) Sterilization of samples: After packaging of coated flasks, they were sent out for gamma irradiation (at the Steris Isomedix, Chester, N.Y. Facility) using a dose range of 11-18 kGy. Upon arrival from gamma irradiation, samples are removed from the aluminum pouch and coating washed off.

vii) Washing protocol for coatings: 150 mL of DI/water is added to the coated flask and the rinsed vigorously for a couple of seconds. This procedure is repeated four to five for all flasks until the majority of the coating has been removed. For coatings that are not completely removed, 100 mL of Di/water is added to the flask bottom and allowed to sit (on coating side) for 5-10 min., to dissolve any remaining coating, then rinsed twice with water. After most of the coating has been removed with water, they are finally rinsed twice with 50 mL of 70% ethanol until all coatings appear completely wash off by physical inspection. Flasks are then allowed to air dry for 2 days prior to being ethanol sanitized for cell culture experiments.

viii) hESC H7 culture: Prior to cell culture all "rinsed off" coatings flasks were ethanol sterilized according to standard in-house protocol prior to cell seeding. H7 cells were sub-cultured into these T-75 flasks including a flask with a Matrigel™ coated surface at a seeding density of $1\times10^6$ cells/flask using cell with a normal karyotype in X-VIVO 10+GF medium. Cell morphology was assessed daily and on day 2 cell contamination was observed. In that respect, cells were stained with crystal violet on day 2 to observe attachment and distribution, thus cell number could not be retrieved.

Results and Discussion

Different combinations of stabilizers such as glycoproteins, sugars, antioxidants, free radical scavengers, amino acids and polyhydric alcohols were strategically formulated into coatings using varying weight percent compositions in their appropriate solvents. As shown in FIG. 4 (a, b) in terms of coatings thickness on the flasks, a thick layer of the respective coating was cast on each flask depending on the coating formulation. Each of the eight (8) flasks containing the different coating formulations had varying degrees of difficulties during washing to remove the coating post gamma irradiation.

Figure 4A:
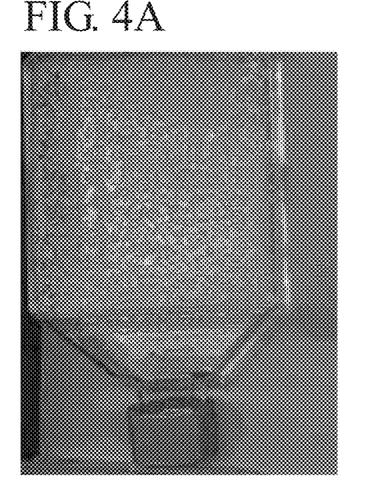
FIG. 4 presents photographs showing representatives of different combinations of antioxidant/stabilizer coatings in VN peptide conjugated acrylate T-75 flasks; All photos were taken prior to packaging for gamma irradiation exposure and consist of (a) Coating 3; (b) Coating 4.
Figure 4B:
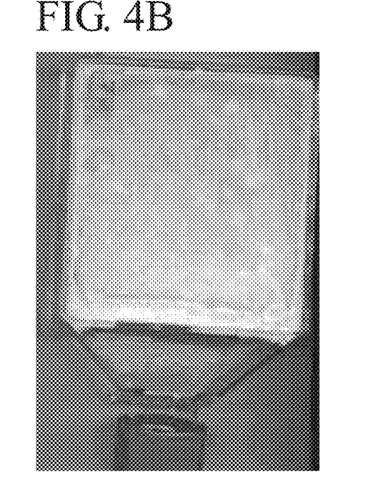
Figure 5A:
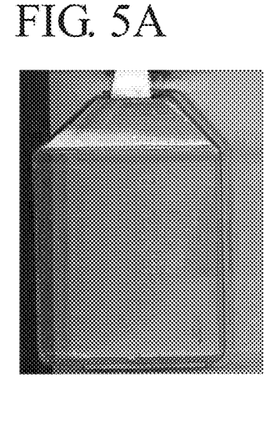
FIG. 5 presents photographs showing representatives of washed off antioxidant/stabilizer coatings in VN peptide conjugated acrylate coated 75 flasks; All photos were taken after the flasks were exposed to gamma irradiation and coatings removed via washing using a series of water and ethanol steps for (a). Coating 3; (b) Coating 4.
Figure 5B:
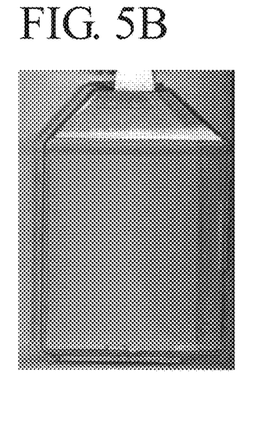
Figure 6A:
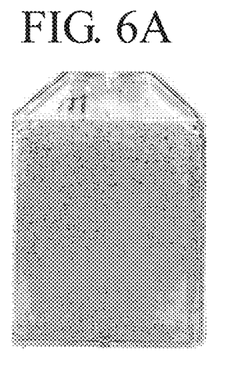
FIG. 6 presents photographs of crystal violet staining (CV staining) showing hESC H7 cell attachment and distribution on "washed off coatings" on peptide conjugated acrylate coated flasks after exposure to gamma irradiation at a dose range of 11-18 kGy as well as control flasks on (a) Coating 1; (b) Coating 2; (c) Coating 3; (d) Coating 4; (e) Coating 5; (f) Coating 6; (g) Coating 7; (h) Coating 8; (i) Ethanol (control) flask; (j) Matrigel (control) flask; —CV staining of cells in flasks was performed at day 2 of cell culture due to contamination; Ethanol sanitized VN peptide acrylate flask and Matrigel surfaces were used as positive controls for the experiment
Figure 6B:
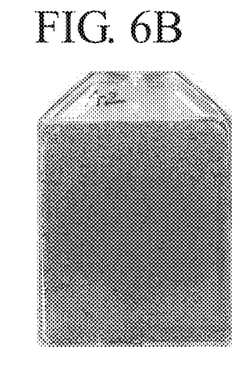
Figure 6C:
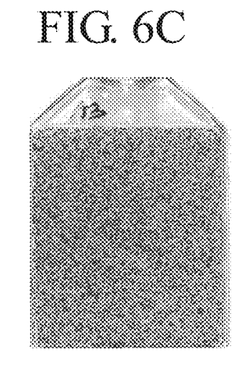
Figure 6D:
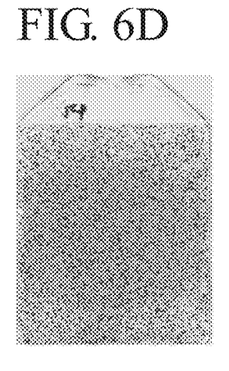
Figure 6E:
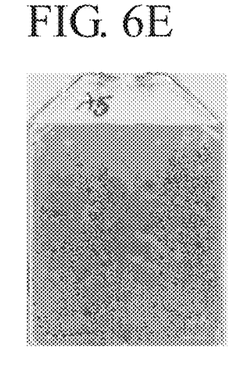
Figure 6F:
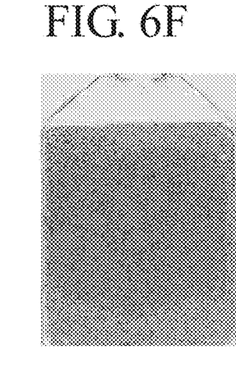
Figure 6G:
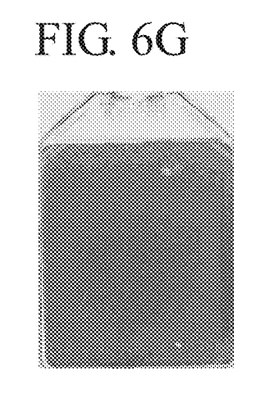
Figure 6H:
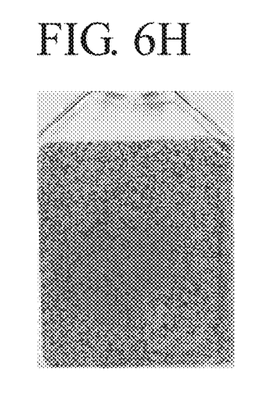
Figure 6I:
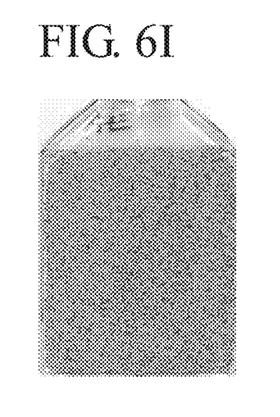
Figure 6J:
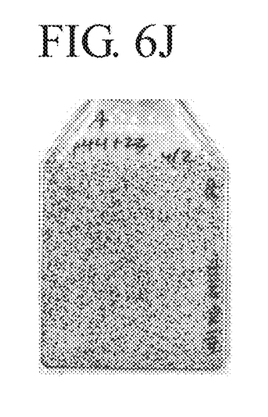

In terms of surface texture of the coatings, a ranged from layers of smooth (FIG. 4b) to very rough or coarse (FIG. 4a) coatings on the bottom was observed. In addition, in terms of transparency, Coating 1 and 2 were transparent (not shown); Coating 7 slightly transparent and Coatings 3, 4, 5, 6 and 8 were opaque (not shown). In regards to the ease of removal of coating during washing (post gamma irradiation), Coatings 2, 5 & 8 were the easiest to wash off using several consecutive washes (2-3 times) of DI/water and 70/30 ethanol:DI/water; Coating 1, 4 & 6 was a little difficult to wash off while Coating 3 & 7 were the most difficult to wash off and required copious amounts of DI/water and 70/30 ethanol: water mixture with very vigorous shaking to ensure that no visible coating fragment were present on the flask.

As shown in FIG. 6(a-j), based on CV staining only Coating 2, 3, 4, 6 and 8 (see FIGS. 6 b, c, d, f and h respectively), showed cell morphology, distribution and relative number comparable to that of those cells cultured on ethanol (i) and Matrigel control flasks (j) while cells on Coatings 1, 5 and 7 (see Figure a, e and g respectively) did not attach or developed embryoid body like morphology.

Based on these results, it is evident that certain combinations of stabilizer coatings were able to offer slightly better protection to the peptides post gamma irradiation than others while a few of them offered no protection as evidenced by the lack of cell attachment after CV staining.

Example 3: Adhesive Peptide Ligands Protecting Peptide Mimetic Surface(s) Against Gamma Irradiation Materials and Methods i) Preparation of acrylate coatings: See Example 1 above for description.

ii) Conjugation of VN peptides on acrylate surfaces: See Example 1 above for description.

iii) Preparation of VN peptide coating solution: A 10 mL 0.5 mM or 1 mM VN coating solution was prepared by weighing out their corresponding masses and dissolving using a 100% 200-proof ethanol as the solvent. Solubility of VN peptide in the ethanol solvent can be classified as a partial to almost completely soluble solution after agitation.

iv) Coating of peptide acrylate T-75 flasks with VN solution: The 10 mL VN solution (different peptide concentration in ethanol) is poured from a conical test tube into the corresponding flasks and capped. The flask is placed of a rocker for at-least 1 hr at room temperature to allow VN solution to evenly coat the bottom of the flaks. Flask is then placed in a hood with cap off for two days to allow ethanol to evaporate after which a layer of VN (white coating) is deposited on the bottom surface of the flask.

v) Packaging of samples for sterilization: All samples for gamma irradiation were individually packaged in an aluminum pouch containing two desiccant packets and vacuum-sealed using a medical grade gas-vacuum sealer.

vi) Sterilization of flasks: After samples have been packaged, they are sent out for gamma irradiation exposure (at the Steris Isomedix, Chester, N.Y. Facility) using a dose range of 11-18 kGy. Upon arrival from Steris, samples are removed from the aluminum pouch and VN peptide coating rinsed off or left intact depending on conditions stated on flasks.

vii) Washing of VN peptide coating on flask: Flasks were washed two to three each consecutively with at-least 50 mL of DI/water followed by a 70/30 ratio of ethanol to water. VN coating washed off easily using both solvents consecutively.

viii) hESC H7 culture: Prior to cell culture all "rinsed off" VN coating flasks were ethanol sterilized according to standard in-house protocol prior to cell seeding. H7 cells were sub-cultured into these T-75 flasks including a flask with a Matrigel™ coated surface at a seeding density of $1\times10^6$ cells/flask using cell with a normal karyotype in X-VIVO 10+GF medium. Cell morphology was assessed daily. On day 2, for cells that showed no attachment, they were CV stained with crystal violet to observe attachment and distribution. For cells that showed attachment, they were CV stained on day 3 to observe attachment and distribution on the T-75 flask.

Results and Discussion

Figure 7:
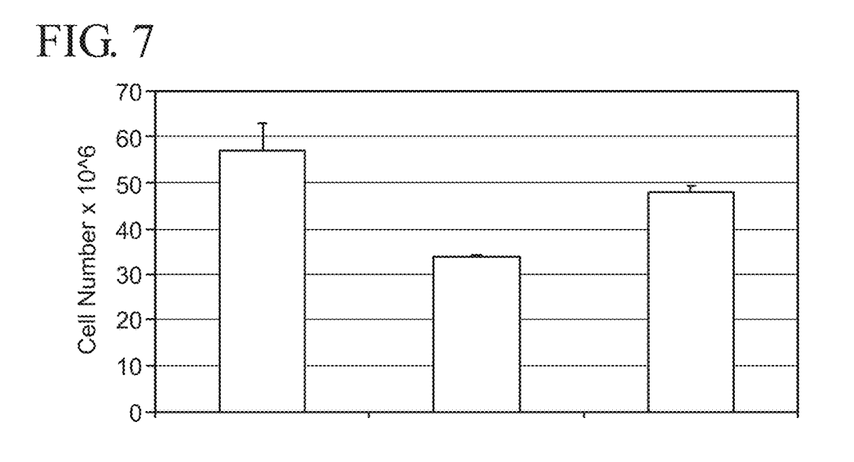
FIG. 7 is a bar graph illustrating cell count/number of hESC H7 cells cultured for 4 days on "Washed off" 1 mM VN peptide coating (third bar) on VN peptide acrylate flask and "washed off" antioxidant (AO) peptide+Methionine coating (second bar) on VN peptide acrylate T-75 flask after exposure to gamma irradiation at a dose range of 11-18 kGy; An ethanol (first bar) sanitized VN peptide acrylate flask was used a positive control.
Figure 8A:
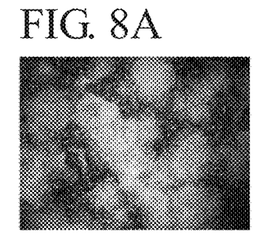
FIG. 8 presents photomicrographs (2.5× images) showing hESC H7 cell morphology cultured on SC-IML VN T-75 flask treated with (a) gamma irradiation with VN coating; (b) gamma irradiation with AO peptide+methionine coating (c) ethanol sanitized (control).
Figure 8B:
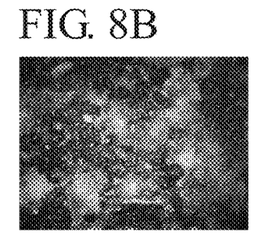
Figure 8C:
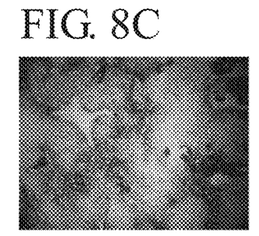

In FIG. 7, the results for hESC H7 cells cultured on post gamma irradiated 1 mM VN peptide conjugated peptide-acrylate flasks that were coated with 1 mM VN coating (in ethanol) (coating washed off post gamma) and new anti-oxidant peptide with 1 wt % methionine coating (coating washed off post gamma) is shown. For this study alone, cells morphology was assessed daily and cells were harvested on day 4 for cell count and viability. For the unwashed coatings (data not shown), cells did not attach, however, for the "washed off" coatings cell number (see FIG. 7) and morphology (see FIG. 8) was comparable to that of those cells on ethanol and Matrigel control flasks.

The new antioxidant peptide sequence contained links of mainly tryrosine and tryptophan both of which are well known amino acid anti-oxidants. From FIG. 7, we observed that there were significantly less cells on "washed off" anti-oxidant+methionine coating compared to the ethanol control. In addition, cell attachment to this surface was comparable to ethanol and matrigel controls, however, colonies became less cystic and detachment was seen after day 3 in culture. In general, this result indicates that 1 mM VN peptide coating (washed) was able to adequately protect the bioactivity of the conjugated VN peptides on the surface of the acrylate, thus making the receptors accessible to the cells.

Figure 9A:
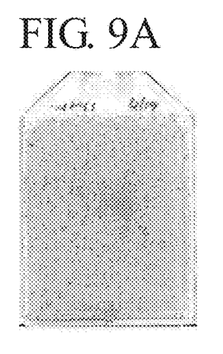
FIG. 9 presents photographs of crystal violet staining (CV staining) showing hESC H7 cell attachment and distribution of different VN peptide concentrations conjugated on acrylate surfaces; and coated with VN peptides as a protecting coating (washed or unwashed coating after exposure to gamma irradiation) (a) 1 mM VN only; (b) 1 mM VN w/pre-gamma ethanol rinse; (c) 0.5 mM VN w/0.5 mM VN coating (unwashed); (d) 1 mM VN w/0.5 mM VN coating (unwashed); (e) 1 mM VN w/0.5 mM VN coating (washed); (f) 1 mM VN only (ethanol sterilized—control flask); (g) Matrigel—control flask.
Figure 9B:
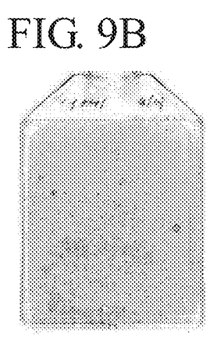
Figure 9C:
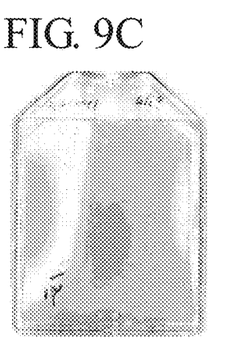
Figure 9D:
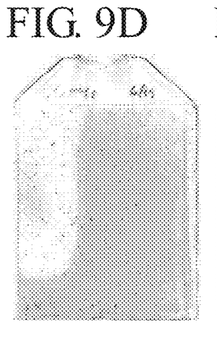
Figure 9E:
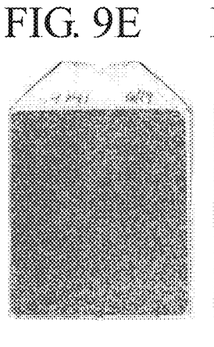
Figure 9F:
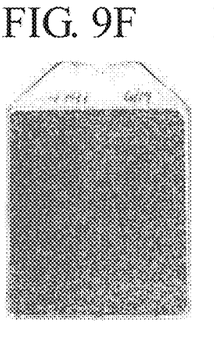
Figure 9G:
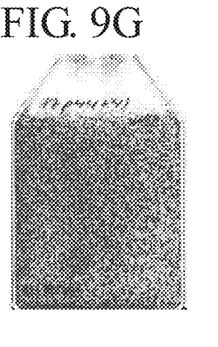
Figure 10A:
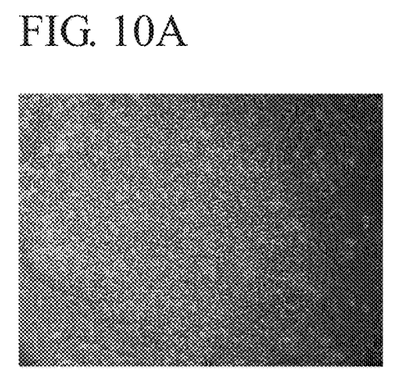
FIG. 10 presents photomicrographs showing hESC H7 cell morphology cultured on (a) gamma irradiated 1 mM VN w/0.5 mN coating (washed); (b) representative gamma irradiated flask with no cell attachment; (c) Ethanol—control flask; (d) Matrigel—control flask.
Figure 10B:
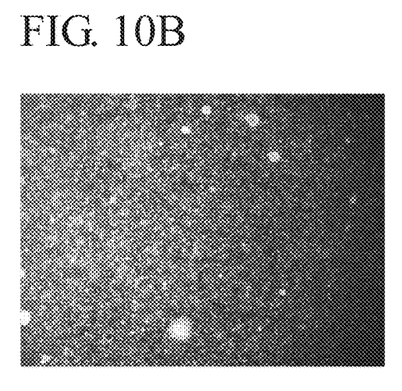
Figure 10C:
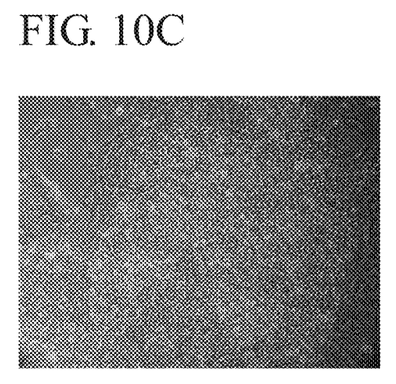
Figure 10D:
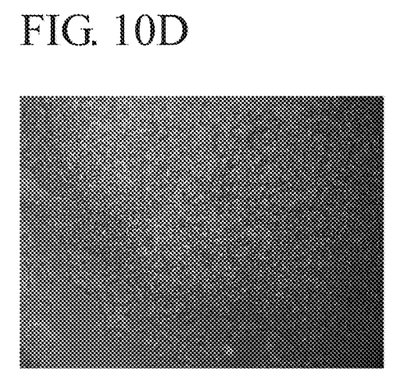

Lower concentrations of VN peptides were also conjugated on the acrylate surfaces using a much lower concentration of VN peptide coating. Likewise, 0.5 mM VN peptide coating was used to protect the surface of a 1 mM VN peptide conjugated peptide as opposed to using a 1 mM VN peptide coating as described earlier above in the results. In FIG. 9a, where only 1 mM VN peptide was conjugated to the acrylate with no VN coating, there was no attachment of cells as observed from the CV staining data. Similar results of no cell attachment was observed in FIG. 9b, where after conjugation flasks was pre-rinsed with ethanol prior to gamma irradiation; FIG. 9c 0.5 mM VN conjugation protected with 0.5 mM VN peptide coating (unwashed coating) and FIG. 9d 1 mM VN conjugation protected with 0.5 mM VN peptide coating (unwashed coating. Cell attachment was only observed on the 1 mM VN peptide conjugation flasks protected with 0.5 mM VN peptide coating that had the VN peptide coating washed off post gamma irradiation, as well as both the ethanol sterilized and Matrigel control flasks.

In general, cell attachment was observed on VN peptide coated flasks that were washed off post gamma irradiation to remove the top coating of VN peptide. This hESC H7 cells could be competing with both the VN peptide coated peptides on the surface and the VN peptide conjugated on the flask surface for attachment. Since the VN peptide coating is washed off by the media upon cell culture, majority of the cells are lost hence there is not enough cells left to attach to the conjugated VN peptides. As shown in the results, the use of VN peptide coating (dissolved in ethanol) was successful in protecting the VN peptide conjugated peptides post gamma irradiation, but only after the VN peptide protective coating has been washed off post gamma to ensure that the hSEC H7 cells receptors can recognize their binding sites on the immobilized VN peptide surfaces. We hope that this VN peptide protective coating can also be used to successfully protect other peptides such as BSP which is usually damaged upon exposure to gamma irradiation.

It will be understood by those of skill in the art that numerous and various modifications can be made without departing from the spirit of the present invention. Therefore, it should be clearly understood that the forms of the present invention are illustrative only and are not intended to limit the scope of the present invention.

We claim:

1. A cell culture substrate modified to protect and stabilize against degradation by gamma irradiation, said cell culture substrate comprising:
   a cell culture surface comprising a (meth)acrylate substrate and a peptide conjugated to the (meth)acrylate substrate, wherein the (meth)acrylate substrate is formed from a composition comprising tetra(ethylene glycol) dimethacrylate, 2-hydroxyethyl methacrylate and 2-carboxyethyl acrylate; and
   a methionine ester covalently bound to the cell culture surface to protect and stabilize said cell culture surface from sterilizing gamma irradiation wherein the peptide is conjugated to the (meth)acrylate substrate via an n-hydroxysuccinimide reactive group; and wherein the methionine ester is conjugated to the (meth)acrylate substrate via an n-hydroxysuccinimide reactive group.

2. The substrate of claim 1, wherein the methionine ester is methionine methyl ester.

3. The substrate of claim 1, wherein the methionine ester forms a protective layer having a thickness of 10 nm to 20 μM.

4. The substrate of claim 1, wherein the peptide is a cell adhesive peptide.

5. The substrate of claim 4, wherein the cell adhesive peptide is vitronectin.

6. The substrate of claim 5, wherein the vitronectin has an amino acid sequence of Ac-Lys-Gly-Gly-Pro-Gln-Val-Thr-Arg-Gly-Asp-Val-Phe-Thr-Met-Pro-NH2 (SEQ ID NO: 1).

7. A method comprising:
   conjugating a peptide to a (meth)acrylate substrate to form a peptide-conjugated substrate, wherein the (meth)acrylate substrate is formed from a composition comprising tetra(ethylene glycol) dimethacrylate, 2-hydroxyethyl methacrylate and 2-carboxyethyl acrylate;
   conjugating a methionine ester to the peptide-conjugated substrate to form a methionine-containing peptide-conjugated substrate; and
   irradiating the methionine-containing peptide-conjugated substrate with gamma radiation to sterilize the methionine-containing peptide-conjugated substrate wherein conjugating the peptide to the (meth)acrylate substrate comprises conjugating the peptide to a n-hydroxysuccinimide reactive group of the (meth)acrylate substrate; and wherein conjugating the methionine ester to the peptide-conjugated (meth)acrylate substrate comprises conjugating the methionine ester to a n-hydroxysuccinimide reactive group of the peptide-conjugated (meth)acrylate substrate.

8. The method of claim 7, wherein conjugating the methionine ester to the peptide-conjugated substrate comprises conjugating the methionine ester to the peptide-conjugated substrate via a residual or un-reacted n-hydroxysuccinimide reactive group remaining after conjugating the peptide to the (meth)acrylate substrate.

9. The method of claim 7, further comprising disposing the methionine ester in a solvent prior to conjugating the methionine ester to the peptide-conjugated substrate, wherein the solvent comprises one or more of lower alcohol, isopropyl alcohol, phosphate buffer solution, boric acid, or deionized water.

10. The method of claim 7, further comprising contacting the methionine-containing peptide-conjugated substrate irradiated with gamma radiation with a surface of a cell culture article.

11. The substrate of claim 1, wherein the methionine ester is a methionine ester salt.

12. The substrate of claim 1, wherein the methionine ester is covalently bound to the cell culture surface via treatment of the cell culture surface with a methionine ester composition comprising methionine methyl ester hydrochloride.

13. The substrate of claim 12, wherein the methionine ester composition consists essentially of methionine methyl ester hydrochloride.

14. The substrate of claim 1, wherein the (meth)acrylate substrate is formed from a composition comprising a volume ratio of 2-hydroxethyl methacrylate:2-carboxyethyl acrylate:tetra(ethylene glycol) dimethacrylate of 80:20:3.

15. The substrate of claim 1, wherein the sterilizing gamma irradiation comprises a dose range of from 11-18 kGy.

\* \* \* \* \*

UNITED STATES PATENT AND TRADEMARK OFFICE
CERTIFICATE OF CORRECTION

PATENT NO. : 10,144,914 B2
APPLICATION NO. : 13/032166
DATED : December 4, 2018
INVENTOR(S) : Dana Craig Bookbinder et al.

It is certified that error appears in the above-identified patent and that said Letters Patent is hereby corrected as shown below:

On the Title Page

In Column 2, item (56), other publications, Line 1, delete "Laborataries," and insert -- Laboratories, --, therefor.

In Column 2, item (57), Abstract, Line 10, delete "for of" and insert -- for --, therefor.

In Column 2, item (57), Abstract, Line 14, delete "glycoprotiens," and insert -- glycoproteins, --, therefor.

On page 2, Column 2, item (56), other publications, Line 5, delete "serium" and insert -- serum, --, therefor.

Signed and Sealed this
Fourteenth Day of April, 2020

Andrei Iancu
*Director of the United States Patent and Trademark Office*

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 1

Lys Gly Gly Pro Gln Val Thr Arg Gly Asp Val Phe Thr Met Pro
1               5                   10                  15